United States Patent [19]

Trick et al.

[11] 4,437,457
[45] Mar. 20, 1984

[54] ARTIFICIAL SPHINCTER WITH IMPROVED PRESSURE CONTROL VALVE

[75] Inventors: Robert E. Trick; Vaughan B. Weeks, both of Racine, Wis.

[73] Assignee: Medical Engineering Corporation, Racine, Wis.

[21] Appl. No.: 372,436

[22] Filed: Apr. 27, 1982

[51] Int. Cl.³ .............................................. A61B 19/00
[52] U.S. Cl. ........................... 128/1 R; 128/DIG. 25; 137/493.2
[58] Field of Search ..................... 137/493.2; 128/1 R, 128/DIG. 25, 344, 346, 685; 604/9

[56] References Cited

U.S. PATENT DOCUMENTS 4,167,952  9/1979  Reinicke et al. ..................... 137/493
4,256,093  3/1981  Helms et al. .......................... 128/1 R Primary Examiner—Edward M. Coven
Assistant Examiner—Christine A. Fukushima
Attorney, Agent, or Firm—Quarles & Brady

[57] ABSTRACT

An improved pressure control valve for a medical device having a hydraulic system comprises a valve housing having an open top and a bottom and an inwardly directed shoulder partially closing the top. A poppet with an upwardly extending stem is mounted in the housing between the top and the bottom. The poppet has a sealing edge mounted on its top about the stem, and there is a calibrated spring urging the poppet towards the open top of the housing so that the sealing edge is in sealing contact with the underside of the shoulder thus closing the valve. The poppet has an internal passage extending therethrough from an inlet in the bottom of the base of the poppet to an outlet in the side of the stem. The outlet in the stem is normally closed by an elastic band which is circumferentially positioned about the stem. The valve can be opened by exerting sufficient force upon the stem or top of the poppet to compress the spring or by a fluid pressure in the internal passage in the poppet which deflects the elastic band so that it no longer closes the outlet of the internal passage.

6 Claims, 5 Drawing Figures

ARTIFICIAL SPHINCTER WITH IMPROVED PRESSURE CONTROL VALVE

The present invention relates to an improved apparatus for reversibly closing a body passage. More particularly, it relates to an artificial sphincter with an inflatable means for controlling the discharge of fluids through the body passage and an improved pressure control valve for the inflatable means.

BACKGROUND OF THE INVENTION

Many persons suffer from a non-functioning or malfunctioning sphincter which controls the discharge of fluids through a body passage. This condition may be caused by congenital malformations, trauma to the sphincter nerves or muscles, or disease of the sphincter nerves or muscles.

One of the most troublesome and embarrassing of such conditions is the malfunctioning of the urethral sphincter. The urethral sphincter retains the urine in the bladder until the sphincter is relaxed to permit passage of urine from the bladder. When the urethral sphincter malfunctions, uncontrollable drainage of urine from the bladder may occur. Obviously, this can be embarrassing to the individual and can restrict his activities.

Attempts have been made in the past to provide an artificial sphincter to substitute for a malfunctioning urethral sphincter or to provide means for controlling artificial openings that have no natural sphincters. Most of the prior art artificial sphincters include inflatable balloons that can be inflated to obstruct or collapse the body passage so that fluid cannot flow through the passage. Representative of such artificial sphincters is that disclosed in the Reinicke U.S. Pat. No. 4,167,952 issued Sept. 18, 1979. The Reinicke device includes a pump, a reservoir for inflating fluid, an inflatable balloon and a relatively complex pressure control valve for controlling the flow of inflating fluid from and to the inflatable balloon.

SUMMARY OF THE INVENTION

It is the primary object of the present invention to provide an artificial sphincter with a relatively simple and inexpensive pressure control valve.

The artificial sphincter of the present invention comprises a closed hydraulic system for controlling the flow through a body passage that includes an inflatable balloon which is normally inflated with hydraulic fluid under pressure to cut off flow through the body passage, a reservoir of inflating fluid, a pump to direct fluid under pressure into the balloon to inflate it and an improved pressure control valve which normally retains the fluid in the inflated balloon at a desired pressure and which can be manually manipulated to deflate the balloon to open the passage to fluid flow.

In the preferred embodiment, the inflatable balloon is an annular cuff which is positioned about the resilient wall of the body passage and which can be inflated to collapse the wall of the body passage to stop flow. In other embodiments, the balloon could be positioned in the body passage and inflated to block flow through the body passage.

BRIEF DESCRIPTION OF THE DRAWINGS

The invention will be hereinafter more fully described with reference to the accompanying drawings in which.

DESCRIPTION OF THE PREFERRED EMBODIMENTS

Figure 1:
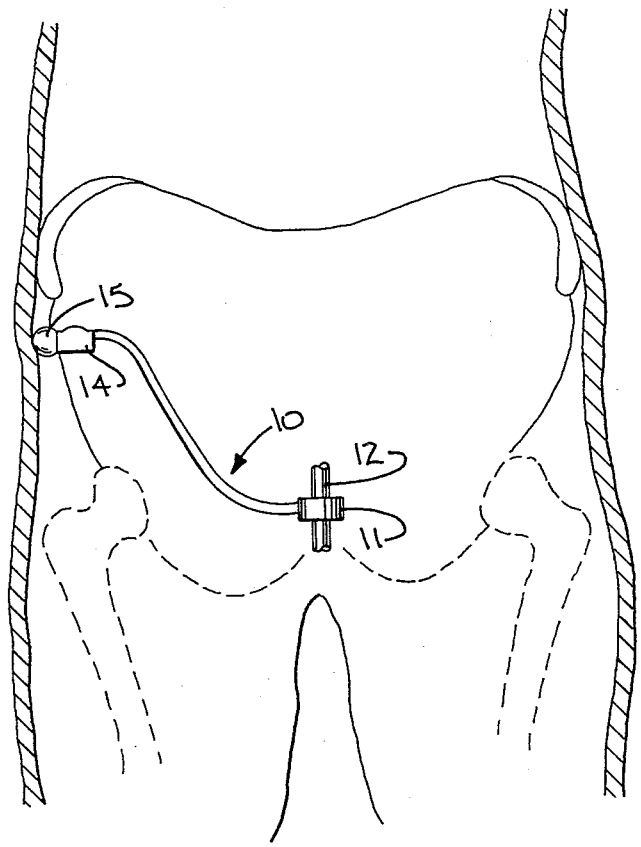
FIG. 1 is a view of the artificial sphincter of the present invention implanted in a human body.

Referring to FIG. 1, there is seen a preferred embodiment of the artificial sphincter of the present invention, generally designated as 10. The sphincter 10 includes a balloon in the form of an annular cuff 11 positioned about a urethra 12 which is normally opened or closed by one or more natural sphincters (not shown). It should be understood that "urethra" as used herein is intended to include both a natural or an artificial urethra or any other suitable natural or artificial body passage.

Figure 2:
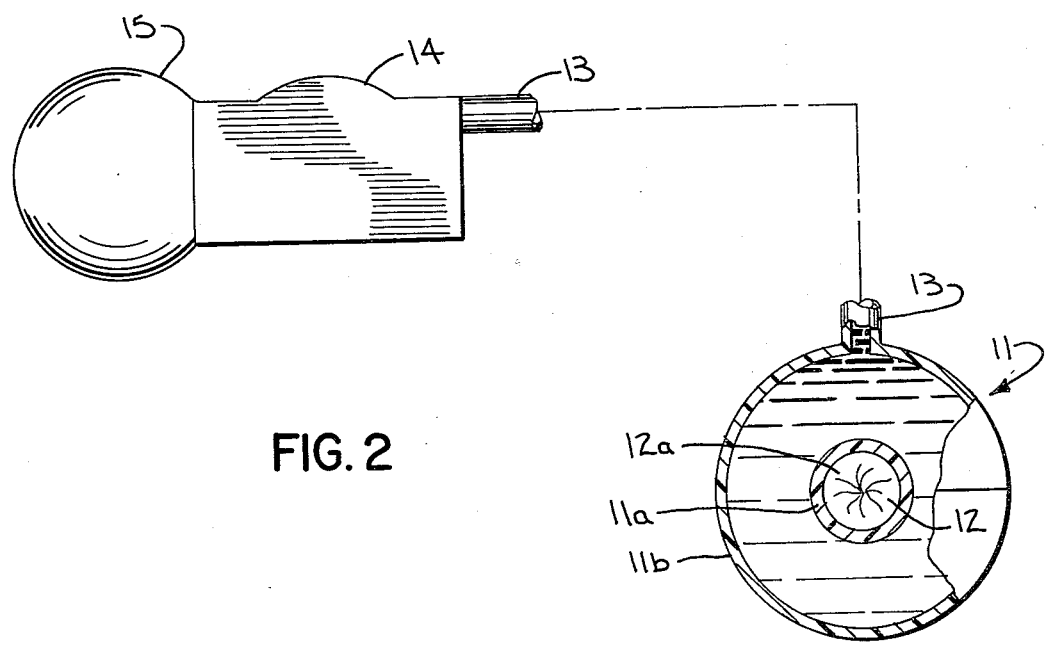
FIG. 2 is an enlarged schematic view showing the cuff inflated and the body passage closed.

Referring to FIGS. 1 and 2, it can be seen that the inflatable cuff 11 is connected by a length of tubing 13 to a valve, generally designated as 14, which is in turn connected to a pressure bulb pump 15. The valve 14 which is positioned between the cuff 11 and the pump 15 is normally closed to prevent fluid from flowing from the cuff 11 to deflate it. When the pump 15 is squeezed, the valve 14 opens to force fluid under pressure into the cuff 11. The valve 14 also serves as a safety valve as it automatically opens to permit fluid to flow from the cuff 11 to the pump 15 when the pressure in the cuff 11 exceeds a predetermined safe inflating pressure.

In FIG. 2, it can be seen that when the cuff 11 is inflated the cylindrical wall 12a of the urethra 12 is collapsed, closing the internal lumen so that no fluid can flow therethrough. When the cuff 11 is deflated the normal resiliency of the wall 12a of the urethra 12 causes the lumen to open.

Although the cuff 11 has been referred to as inflatable, it does not have to be elastic as the term is normally understood. However, it is necessary that the cuff 11 have a readily deformable inner wall 11a. The deformable wall 11a is preferably thinner and thus more elastic and deformable than the outer wall 11b. However, it will be appreciated that the difference in deformability of the walls 11a and 11b can be achieved by other techniques than varying the thickness, e.g. making 11b of a less flexible or less elastic material.

The operation of the artificial sphincter 10 and the valve 14 will now be described in connection with FIGS. 1 to 5.

Figure 3:
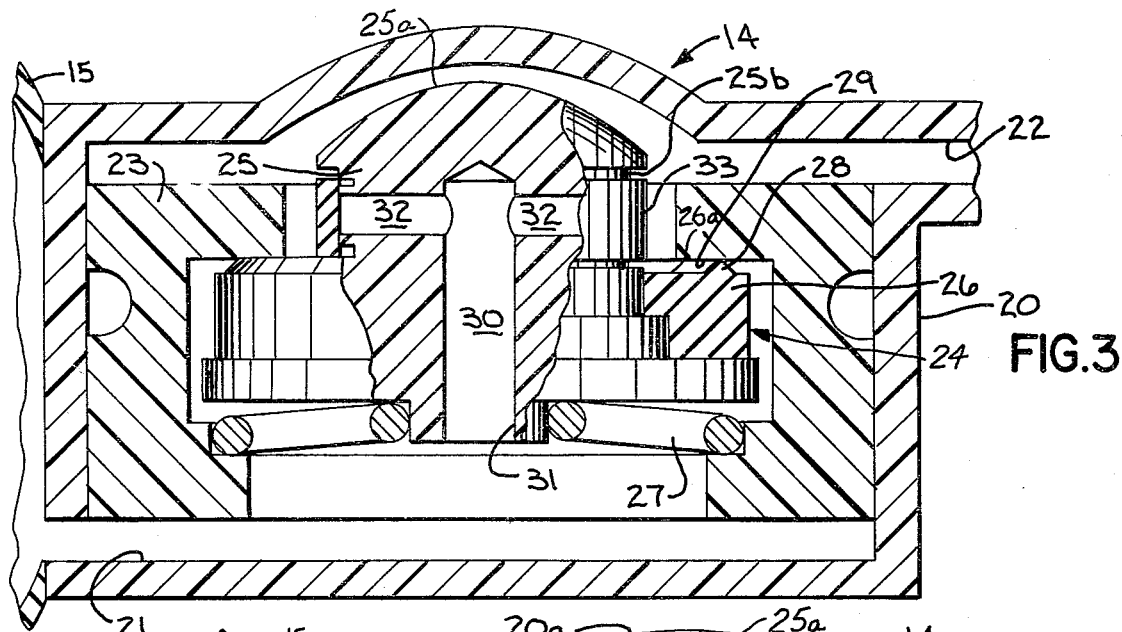
FIG. 3 is a sectional view of the improved pressure control valve of the present invention in its normally closed position retaining fluid under pressure in the inflated cuff with the body passage closed.

The cuff 11 is normally inflated as seen in FIG. 2 causing the wall 12a of the urethra 12 to be collapsed closing the lumen to fluid flow. When the cuff 11 is inflated the internal components of the valve 14 are as seen in FIG. 3 and the valve 14 is closed. When it is desired to empty the bladder (not shown) the cuff 11 is deflated to permit the natural resiliency of the wall 12a of the urethra 12 to cause the lumen to open. The cuff 11 is deflated by manually squeezing the valve 14, as seen in FIG. 4, to permit the fluid under pressure in the cuff 11 to flow out of the cuff 11 through the valve 14 to the pump 15.

Figure 5:
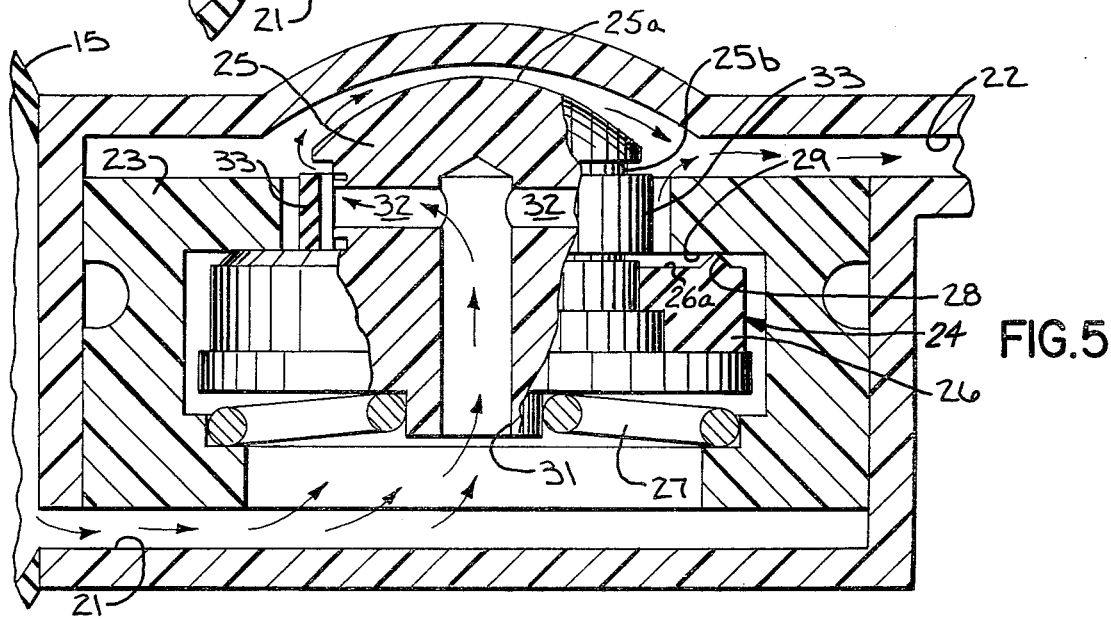
FIG. 5 is a sectional view of the valve showing position of the valve components when the inflating fluid is being pumped under pressure to the cuff.

The refilling or reinflation of the cuff 11 after the flow of fluid through the urethra 12 has ceased is accomplished by manually squeezing the pump 15 to force fluid under pressure through the valve 14 in the direction shown by arrows in FIG. 5. It will be appreciated that a variety of pump mechanisms other than the pressure bulb shown in the drawing can be used.

Figure 4:
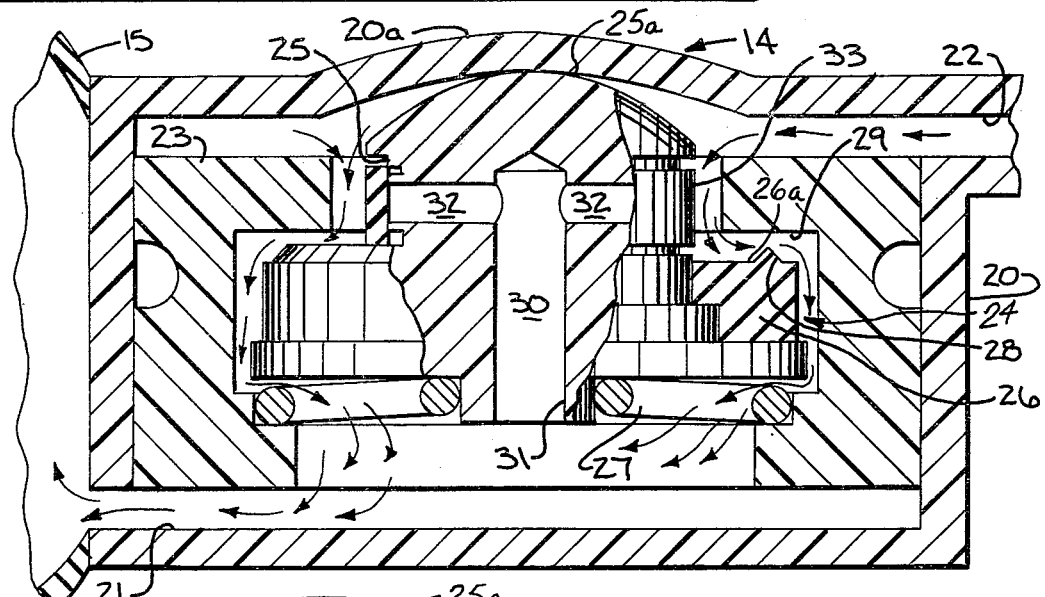
FIG. 4 is a sectional view of the valve when manually actuated to deflate the cuff and open the body passage.

As seen best in FIGS. 3, 4 and 5, the pressure control valve 14 includes an outer jacket 20 having an inlet 21 which communicates with pump 15. An outlet 22 of the outer jacket 20 communicates via tubing 13 with the cuff 11.

Referring to FIG. 3, it can be seen that positioned in the jacket 20 between the inlet 21 and the outlet 22 is a valve housing 23. A poppet 24 having a stem 25 is movably mounted in the housing 23. The poppet 24 which has an annular seal 26 positioned about the stem 25 is supported within the housing 23 by a calibrated spring 27 so that the sharp edge 28 of the seal 26 seats against the underside of an upwardly directed shoulder or flange 29 which partially closes the top of the housing 23. The force of the spring 27 on the poppet 24 normally keeps the sharp edge 28 of the seal 26 in fluid tight contact with the flat underside of the flange 29 so that the valve 14 is closed and no fluid can flow from the inlet 21 to the outlet 22 or vice versa.

As seen in FIG. 4, the valve 14 can be opened to permit fluid to flow from the cuff 11 to the pump 15 by manually exerting a force on the jacket 20 at point 20a to cause that portion of the jacket 20 to deflect and contact the top 25a of the stem 25 of the poppet 24. Further force on point 20a causes the poppet 24 to move towards and compress the spring 27 and the sharp edge 28 to move from sealing engagement with the underside of the flange 29 of the housing 23. As a result, as shown by the arrows, fluid flows through valve 14 from the cuff 11 via tubing 13 to the pump 15. When the force on the jacket point 20a and the stem 25 is relieved the calibrated spring 27 forces the sharp edge 28 back into sealing arrangement with the flat underside of the flange 29 closing the valve 14 and cutting off flow from the inlet 21 to the outlet 22.

The valve 14 also serves as a safety valve which prevents the fluid pressure in the cuff 11 from exceeding a safe, predetermined pressure. When the fluid pressure in the cuff 11 as sensed by the top surface 26a of the seal 26 of the poppet 24 exceeds the force of the calibrated spring 27, the sharp sealing edge 28 is moved out of sealing engagement with the underside of the shoulder 29. Fluid then flows through the valve 14 from the cuff 11 to the pump 15 in the direction of the arrows shown in FIG. 4 until a safe pressure is reached in cuff 11 whereupon the calibrated spring 27 moves the poppet 24 toward the flange 29 and causes the sharp edge 28 to once again come into sealing engagement with the underside of the flange 29.

In the preferred embodiment of the improved valve 14 seen in FIGS. 3, 4 and 5, there is an internal passage 30 which extends vertically from an inlet 31 in the bottom of the base of the poppet 24 up through the stem 25 and then radially outward to an outlet 32 in the side of the stem 25. The outlet 32 is normally closed by an elastic band 33 which is positioned in a groove 25b about the stem 25. When the band 33 is deflected, fluid can flow through the passage 30 from the inlet 31 to the outlet 32. Thus fluid in the pump 15 can flow under pressure to the cuff 11.

When the pump 15 is squeezed to refill the cuff 11 and close the urethra 12, the pressure of fluid from the pump 15 will exceed the elasticity and compressive force of the band 33 and deflect the band 33 so that fluid will flow through the passage 30 out the outlet 32 and into the cuff 11 as shown by the arrows in FIG. 5. When the squeezing is stopped, the elastic band 33 reseals the outlet 32 and the valve 14 is again closed as seen in FIG. 3.

The diameter and thickness or elasticity of the elastic band 33 can be varied to provide a band that has the desired elasticity and compressive strength so that it will seal the outlet 32 when the squeezing of the pump 15 stops. The material of the band can be silicone, rubber or any other suitable elastomer.

The spring 27 may be of stainless steel. It is calibrated so that it compresses when a predetermined force or load is exerted upon it.

All of the parts and components of the artificial sphincter and valve are preferably made of or covered with medical grade silicone rubber which is non-reactive, nontoxic and well tolerated by the adjacent organic tissues. Silicone rubber is preferred because it is quite resistant to wear and remains functional for long periods of time. However, other suitable materials possessing desirable properties may also be employed.

Prior to implanting the artificial sphincter 10, it is initially filled with hydraulic fluid under a slight pressure. The fluid preferred for this purpose is of physiological saline. The hydraulic fluid selected must be physiologically compatible with body tissue and body organs in the event that a leak would develop in the system.

The apparatus of the present invention preferably is implanted completely within the patient's body. The valve 14 and pump 15 preferably are positioned just below the skin of the patient so that they can be operated from outside by depressing the valve 14 or squeezing the pump 15 as described. This may be done by making a suitable incision through the skin so as to provide access to the abdominal cavity. With the abdominal cavity opened, the urethra can be exposed and the cuff properly positioned. The other components may be arranged generally as shown in FIG. 1 and the abdominal cavity surgically closed. The manner of the implantation described is generic for both males and females. The systems disclosed are sufficiently versatile to allow implanting in various regions of the body. For example, for some male patients it may be preferable to implant the valve 14 and pump 15 in the patient's scrotum.

It will be appreciated by those skilled in the art that the foregoing description of the preferred embodiments for use in controlling the urethra has been for purposes of illustration only. The apparatus and the method of the present invention can be used to control flow through other body passages such as the colon. Therefore, it is intended that the scope of the invention not be limited except by the claims which follow.

We claim:

1. A pressure control valve for a medical device including a hydraulic system, said valve comprising:
    (a) a valve housing, said housing having an open top and open bottom and an inwardly directed shoulder partially closing said top;

(b) a poppet mounted in said housing between the top and bottom, said poppet having a base, an upward extending stem, and a sealing edge on the top of said poppet base, said sealing edge being circumferentially positioned about said stem, said poppet also having an internal passage extending therethrough and leading from an inlet in the base to an outlet in the side of the stem;

(c) an elastic band positioned circumferentially about the stem of the poppet removably closing the outlet of said internal passage, said band being deflectable by an increase in fluid pressure in said internal passage to open said outlet; and (d) yieldable means for urging said poppet towards said open top so that said stem extends out of said housing and said sealing edge is in sealing contact with the underside of said shoulder closing off fluid flow through the housing.

2. The valve of claim 1 in which the yieldable means for urging said poppet towards the open top is a calibrated spring.

3. A medical device including a hydraulic system and a pressure control valve in which the pressure control valve comprises:

(a) a valve housing having an open top and a bottom and an inwardly directed flange partially closing said top;

(b) a poppet mounted in said housing between the top and the bottom, said poppet having an upwardly extending stem and a base with a sealing edge mounted on the top of said base, said sealing edge being positioned circumferentially about said stem, said poppet also having an internal passage extending from an inlet through the base and to an outlet in the side of the stem;

(c) an elastic band removably closing the outlet of the passage in the stem, said band being deflectable by an increase in fluid pressure in the internal passage to open said outlet; and (d) yieldable means for urging said poppet towards said open top so that the sealing edge on the top of the poppet is normally in sealing contact with the underside of said shoulder and the stem extends above the top of said housing so that manual pressure can be exerted upon the stem to open the valve or the valve can be opened by a hydraulic pressure.

4. The device of claim 3 in which the yieldable means for urging the poppet towards the open top is a calibrated spring.

5. An artificial sphincter comprising an inflatable balloon for closing a body passage, a pump for transferring inflating fluid to the balloon to pressurize and inflate it to collapse the body passage, and a pressure control valve for controlling the pressure in the balloon, said pressure control valve comprising:

(a) a valve jacket having an inlet and an outlet, said inlet communicating with the pump, and the outlet communicating with the inflatable balloon;

(b) a valve housing positioned in said jacket, said housing having an open top and bottom and an inwardly directed shoulder partially closing said top;

(c) a poppet mounted in said housing between the inlet and the outlet; said poppet having an upwardly extending stem and a base with a sealing edge mounted on the top of said base, said poppet also having an internal passage extending from an inlet through the base and to an outlet in the side wall of the stem;

(d) an elastic band circumferentially positioned about the stem and removably closing the outlet of the passage; and (e) yieldable means exerting a force upon said poppet urging it toward the open top of the housing so that the sealing edge will be in sealing contract with the underside of the shoulder closing said valve.

6. The artificial sphincter of claim 5 in which the yieldable means is a precalibrated spring which permits the valve to open when sufficient force is exerted on the top of the poppet and which automatically closes the valve when the force on the top of the poppet is less than that required to compress the spring.

* * * * *